United States Patent [19]

Piccolo et al.

[11] Patent Number: 4,670,603

[45] Date of Patent: Jun. 2, 1987

[54] PROCESS FOR THE PREPARATION OF ARYL ALKYL KETONES

[75] Inventors: Oreste Piccolo, Leghorn; Giuseppina Visentin, Monza; Pietro Blasina, Milan; Franca Spreafico, Como, all of Italy

[73] Assignee: Blaschim S.p.A., Milan, Italy

[21] Appl. No.: 779,797

[22] Filed: Sep. 24, 1985

[30] Foreign Application Priority Data

Sep. 24, 1984 [IT] Italy ............................... 22800 A/84
May 17, 1985 [IT] Italy ............................... 20768 A/85

[51] Int. Cl.$^4$ .............................................. C07C 45/46
[52] U.S. Cl. ...................................... 568/319; 568/322
[58] Field of Search ........................ 568/323, 322, 319

[56] References Cited

U.S. PATENT DOCUMENTS 4,061,779 12/1977 Lake et al. ........................... 568/319
4,593,125 6/1986 Davenport et al. .................. 568/323

FOREIGN PATENT DOCUMENTS 2209692 9/1973 Fed. Rep. of Germany ...... 568/323
54-135756 10/1979 Japan ................................... 568/323
59-51234 3/1984 Japan ................................... 568/323

OTHER PUBLICATIONS

Olah, "Friedel Crafts & Related Reactions", vol. III, pp. 20 to 23 (1964).
Cavrini et al., Chem. Abst., vol. 97, #38629c (1982).
Nippon Soda, Chem. Abst., vol. 101, #151604e (1984).
Olah, "Friedel-Crafts & Related Reactions", vol. 1, Interscience Publishers, pp. 317-321 (1963).

Primary Examiner—James H. Reamer
Attorney, Agent, or Firm—Berman, Aisenberg & Platt

[57] ABSTRACT

Preparation of aryl alkyl ketones by reaction of an aryl compound with an aliphatic acid and/or a functional derivative thereof in anhydrous hydrofluoric acid.

7 Claims, No Drawings

PROCESS FOR THE PREPARATION OF ARYL ALKYL KETONES

This invention relates to a process for the preparation of aryl alkyl ketones by reacting an aryl compound with an aliphatic acid or a functional derivative thereof or of their mixtures in anhydrous hydrofluoric acid.

More particularly, the process of this invention may be represented by the following diagram:

$$ArH + Y-CO-CHX-R \longrightarrow Ar'-CO-CHX-R$$
$$\quad\quad I \quad\quad\quad\quad\quad\quad\quad\quad\quad\quad II$$

wherein
ArH is 2-methoxy-naphthalene;
Ar' is 6'-methoxy-2'-naphthyl;
Y is OH, halogen or O—CO—CHX—R;
X is hydrogen or halogen; and
R is hydrogen or methyl.

The compounds of formula II are useful as intermediates for the preparation of Naproxen by rearrangement of halo ketals (European Pat. No. 0035305) or by the Darzens reaction (JP Kokai 75/18448, C.A. 83, 789545x, 1975).

It is known that acylation of 2-methoxy-naphthalene with derivatives of aliphatic acids, more particularly with aliphatic acyl halides, in the presence of Lewis acids according to the Friedel-Crafts reaction leads to different products depending on the solvent used (J. Chem. Soc. (C), 1966, 181-5).

In particular, the 2-methoxy-6-acyl-naphthalenes may be prepared only in nitrobenzene (loc. cit.; Org. Synthesis, 53, 5, 1973), in nitroalkanes (C.A. 64, 12620 f, 1966) or in polyphosphoric acids (C.A. 58, 1546 gh, 1963).

Said processes have however serious drawbacks when it is sought to carry them out on an industrial scale.

Carrying out of the process in nitrobenzene or nitroalkanes, in addition to the well known problems connected with toxicity of the nitro derivative, also involves considerable labor and energy costs because of the type of operations required, i.e. careful temperature control during addition of the reactants and during quenching of the aluminum chloride, filtration and discharge of the aluminium derivatives, and recovery of the nitro derivative by distillation. Lastly, this process may be carried out only using acid halides because the aliphatic acids do not react, and the anhydrides require greater quantities of both Lewis acid and solvent.

Polyphosphoric acid is difficult to use because has a pasty consistency, requires high temperatures, cannot be recovered, and is difficult to dispose of.

It has now been found that the compounds of formula II may be readily prepared in accordance with the reaction diagram indicated above in anhydrous hydrofluoric acid.

A first advantage of this process is that, differently from known processes, the acylating agent of formula I can be not only a halide but also the acid or the anhydride of the acid or acid/anhydride, acid/halide, anhydride/halide mixtures or ternary mixtures.

A second advantage of this process is that it does not require the use of aluminium chloride or other conventional catalyst of the Friedel-Crafts reaction; their possible addition does not affect the yields.

A further advantage of the process according to this invention is that hydrofluoric acid is easily recovered by distillation because of its low boiling point (19.5° C.). The possible presence of aliphatic acid or its functional derivatives in the hydrofluoric acid thus recovered is not an obstacle to recycling it.

Another advantage of this process is that no substantial racemization occurs when an optically active acylating agent (of formula I, where X is chlorine and R is methyl) is used thus obtaining an optically active compound of formula II which is a suitable intermediate for stereospecific preparation of Naproxen according to known techniques.

Owing to its simplicity and great flexibility the process of this invention lends itself to numerous variants without departing from the inventive idea.

The following examples will serve to illustrate this invention without however limiting it.

EXAMPLE 1

1-(6'-methoxy-2'-naphthyl)-propane-1-one 56.7 g (0.43 mol) of propionic anhydride and 50 g (0.32 mol) of 2-methoxy-naphthalene were added to 200 ml of anhydrous hydrofluoric acid. The reaction mixture was stirred at 19° C. for 28 hours and then poured into ice and extracted with methylene chloride (3×200 ml).

The combined organic extracts were neutralized with a 10% aqueous solution of sodium hydroxide and then washed with water, dried over sodium sulphate and concentrated.

The residue (63 g) contained 84% of the desired product (yield, 77%) and less than 1% of the isomer 1-(2'-methoxy-1'-naphthyl)-propane-1-one.

Pure 1-(6'-methoxy-2'-naphthyl)-propane-1-one was obtained by crystallization of the crude with suitable solvent such as methanol, heptane, toluene, and their mixtures.

Similar results were obtained by:
carrying out the reaction at 37° C. for 8 hours (yield, 80%);
reducing the quantity of propionic anhydride to 47.8 g (0.37 mol) and adding 15 g (0.20 mol) of propionic acid and carrying out the reaction at 37° C. for 8 hours (yield, 74%);
substituting the propionic anhydride with a mixture of 41 g (0.44 mol) of propionyl chloride and 33 g (0.44 mol) of propionic acid (yield 77%);
substituting the propionic anhydride with propionic acid (yield, 34%).

EXAMPLE 2

1-(6'-methoxy-2'-naphthyl)-ethane-1-one

Working as described in the above Example 1, but replacing the propionic anhydride with acetic anhydride (43.9 g, 0.43 mol), 52.5 g of crude containing 89% 2-(6'-methoxy-2'-naphthyl)ethane-1-one (yield, 86%) were obtained and then purified by crystallization.

EXAMPLE 3

1-(6'-methoxy-2'-naphthyl)-propan-1-one

To 225 g of anhydrous hydrofluoric acid, 49.5 g (0.57 mol) of propionyl chloride and then 70 g (0.44 mol) of 2-methoxy-naphthalene in 90 g of anhydrous hydrofluoric acid were added at 19° C.

The reaction mixture was maintained at 40° C. for 71 hours and then worked up as disclosed in Example 1.

Yield, 70 g (73%).

EXAMPLE 4

(S) 1-chloroethyl-(6'-methoxy-2'-naphthyl)-ketone

To 460 g of anhydrous hydrofluoric acid, 38.3 g (0.3 mol) of (S) 2-chloro-propionyl chloride $[\alpha]_D^{25} = +1.64°$ (neat, l=1) (optical purity, 31%) and then 32 g (0.2 mol) of 2-methoxy-naphthalene in 50 ml of methylene chloride were added.

The reaction mixture was maintained at 20° C. for 22 hours and then worked up as disclosed in Example 1.

The residue was purified on a silica gel column (eluent, toluene); 4 g of (S) 1-chloroethyl-(6'-methoxy-2'-napthyl)ketone was obtained having $[\alpha]_D^{25} + 31.2°$ (c=1%, chloroform) optical purity 27%.

We claim:

1. A process for preparing an aryl alkyl ketone of the formula $$Ar'-CO-CHX-R \qquad (II)$$

wherein
  Ar' is 6'-methoxy-2'-naphthyl,
  X is hydrogen (—H) or halogen, and
  R is hydrogen (—H) or methyl,
which comprises reacting 2-methoxynaphthalene in anhydrous hydrofluoric acid with at least one compound of the formula $$Y-CO-CHX-R \qquad (I)$$

wherein
  Y is —OH, halogen or —O—CO—CHX—R, and
  R and X have their previously-ascribed meanings.

2. A process according to claim 1 which comprises reacting 2-methoxynaphthalene with a mixture of compounds of formula I.

3. A process according to claim 1 wherein Y is —OH.

4. A process according to claim 1 wherein Y is halogen.

5. A process according to claim 1 wherein Y is —O—CO—CHX—R.

6. A process according to claim 1 wherein R is —H.

7. A process according to claim 1 wherein R is methyl.

* * * * *